United States Patent [19]
Bader et al.

[11] Patent Number: 4,835,248
[45] Date of Patent: May 30, 1989

[54] BIOLOGICALLY DEGRADABLE POLYAMIDE FOR DEPOT PREPARATIONS HAVING CONTROLLED RELEASE OF THE ACTIVE COMPOUND

[75] Inventors: Hubert Bader, Mainz; Diether Rüppel; Axel Walch, both of Frankfurt am Main; Michael Magerstädt, Liederbach, all of Fed. Rep. of Germany

[73] Assignee: Hoechst Aktiengesellschaft, Frankfurt am Main, Fed. Rep. of Germany

[21] Appl. No.: 49,164

[22] Filed: May 13, 1987

[30] Foreign Application Priority Data

May 15, 1986 [DE] Fed. Rep. of Germany ....... 3616320
Mar. 7, 1987 [DE] Fed. Rep. of Germany ....... 3707369

[51] Int. Cl.$^4$ .............................................. C08G 69/10
[52] U.S. Cl. ..................................... 528/328; 424/78; 525/420; 528/310; 528/327; 528/341; 528/345
[58] Field of Search ............... 528/328, 327, 341, 345, 528/310

[56] References Cited

U.S. PATENT DOCUMENTS

| 3,297,033 | 1/1967 | Schmitt et al. | 128/335.5 |
| 3,371,069 | 2/1968 | Miyamae et al. | 260/78 |
| 3,773,919 | 11/1973 | Boswell et al. | 424/19 |
| 4,069,307 | 1/1978 | Higuchi et al. | 424/22 |
| 4,093,709 | 6/1978 | Choi et al. | 424/19 |
| 4,180,646 | 12/1979 | Choi et al. | 528/153 |
| 4,304,767 | 12/1981 | Heller et al. | 424/78 |
| 4,745,161 | 5/1988 | Saudek et al. | 528/328 |

FOREIGN PATENT DOCUMENTS

| 12139 | 6/1964 | Japan | 528/328 |

OTHER PUBLICATIONS

Rosen et al., Bioerodible Polyanhydrides for Controlled Drug Delivery, Biomaterials, vol. 4, 1983, pp. 131–133.

Primary Examiner—Harold D. Anderson
Attorney, Agent, or Firm—Finnegan, Henderson, Farabow, Garrett & Dunner

[57] ABSTRACT

Polyamides in which amino acids are incorporated in the polymer backbone via two amino or carboxyl groups and which carry in the α-position to the amide structure a functional group which is responsible for degradation and active compound release are highly suitable for the preparation of biologically degradable active compound depot preparations having controlled release of the active compound.

6 Claims, 1 Drawing Sheet

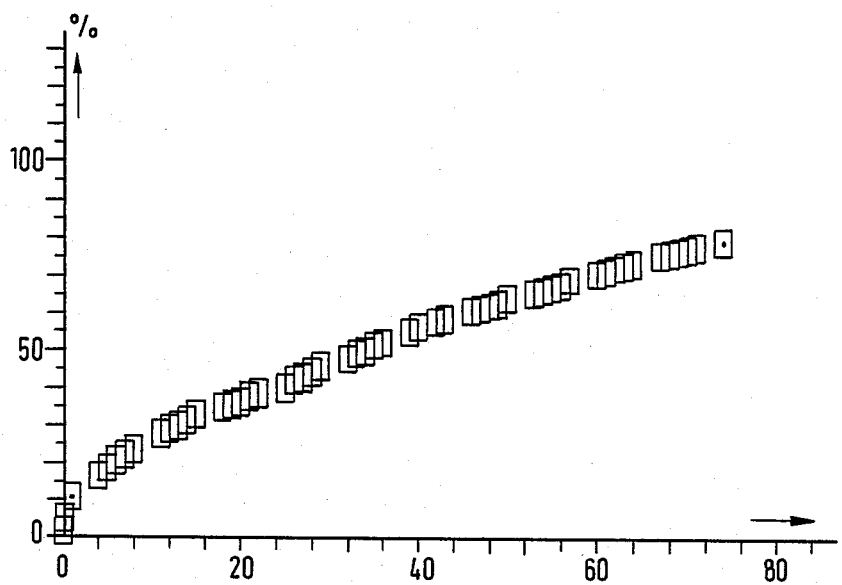

BIOLOGICALLY DEGRADABLE POLYAMIDE FOR DEPOT PREPARATIONS HAVING CONTROLLED RELEASE OF THE ACTIVE COMPOUND

Long-duration controlled release of the active compound is of great topicality due to the increasing importance of chronic disorders and long-term oriented therapy concepts in human and veterinary medicine.

Medicament release systems in which the active compound is dispersed in a nondegradable polymer matrix and is liberated by diffusion are described in U.S. Pat. No. 4,069,307. When the active compound reservoir is exhausted, such implants must, however, be removed surgically from the organism.

In biologically degradable medicament release systems, such as specified in U.S. Pat. No. 4,093,709, the active compound is dispersed in a biodegradable polymer which releases the active compound on degradation. Typical biologically degradable polymers which have been most investigated according to the state of the art are homopolyesters and copolyesters, in particular of lactic acid and glycolic acid, as are described in U.S. Pat. Nos. 3,773,919 and 3,297,033 respectively. A disadvantage is, inter alia, the low or poorly controllable swellability of the polyesters in the physiological environment, which hinders permeation of the active compounds incorporated in the implant and causes an only low liberation rate after the initial "burst effect". Recently, polyacetals and polyketals have been described in U.S. Pat. No. 4,304,767, polyanhydrides have been described by H. G. Rosen et al., Biomaterials 4, 131 (1983), and polyorthoesters have been described in U.S. Pat. No. 4,180,646; all these compounds were developed as biologically degradable polymers for use as implant materials. Due to the lack of further functional groups, similar to the polyesters mentioned, the degradation of these polymers is only determined by the hydrolytic resistance of the carbonyl function in the main polymer chain. In addition, such polymers do not have adequate stability for implantation periods of months. As further classes of polymers, polyamides, in particular polyamino acids, have been described in U.S. Pat. No. 3,371,069 as bioresorbable implant materials. However, the industrial preparation of polyamino acids requires the use of expensive protected amino acids, relatively large amounts of highly toxic phosgene, the removal of the protecting groups and the chemical modification of the polymers obtained.

Surprisingly, it has been found that polyamides in which amino acids are incorporated in the polymer backbone via two amino or carboxyl groups and which carry in the α-position to the amide structure a functional group which is responsible for degradation and active compound release are highly suitable for use as degradable medicament implants having controlled release of the active compound. These biologically degradable polymers are obtained by polycondensation of physiologically and pharmacologically acceptable diamines with just such dicarboxylic acids. In vivo, these polymers are metabolized into nontoxic, nonallergenic and nonimmunogenic compounds and are excreted.

The invention thus relates to:

(1) A biologically degradable polyamide in which amino acids are incorporated into the polymer backbone via two amino or carboxyl groups and which carry in the α-position to the amide structure a functional group which is responsible for degradation and active compound release, with (I) repeating units of the diamino compound from the group comprising
the monomeric compound of the general formula Ia,

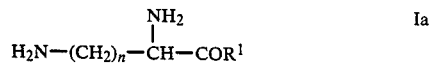

in which

R$^1$ denotes a physiologically acceptable, hydrolyzable alkoxy group, having up to 18 carbon atoms, which can optionally be substituted by physiologically acceptable side groups, or denotes a physiologically acceptable, hydrolyzable alkylamino or aralkylamino group, or denotes a hydroxyl group, and n is 3 or 4, and/or the monomeric compound which is produced by esterification of aminoethanol with the dicarboxylic acids of the citrate cycle, and/or the monomeric compound of the general formula Ib,

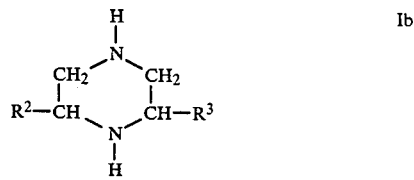

in which R$^2$ and R$^3$, independently of one another, denote hydrogen or methyl, and (II) repeating units of the dicarboxylic acid compounds from the group comprising
the monomeric compound of the general formula IIa,

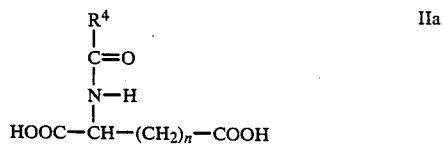

in which

R$^4$ denotes an alkyl group having 1 to 3 carbon atoms, and n denotes 1 or 2, and/or the monomeric straight-chain, saturated or monounsaturated dicarboxylic acids having 2–10 carbon atoms, and/or the monomeric compound which is produced by esterification of the dicarboxylic acids of the citrate cycle with diols of the general formula IIb,

in which

R$^6$ and R$^7$, independently of one another, denote hydrogen or a methyl group, and m is a number in the range 1 to 100, or by amidation with diamines of the general formula Ib mentioned.

(2) The process for the preparation of the abovementioned polyamide, wherein one or more of the diamino and dicarboxylic acid compounds mentioned under (1) are polycondensed.

(3) The use of the abovementioned polyamide for encapsulation of biologically active substances.

(4) The use of the abovementioned polyamide as a degradable depot preparation of the active compound having controlled release of the active compound.

In the following, the invention is described in detail and defined in the claims.

As diamino compound of the formula Ia, esters of ornithine and lysine with physiologically acceptable, hydrolyzable alkoxy groups which have up to 18 carbon atoms are employed. Although esters with higher alkoxy groups can also be used, the polymerization becomes more difficult with increasing chain length. These alkoxy groups can, if appropriate, be substituted by hydrolyzable, physiologically acceptable side groups. The following alkoxy groups are suitable, for example:

n- or iso-$(C_1-C_{18})$alkoxy, preferably methoxy, ethoxy, butyloxy, octadecyloxy and isopropyloxy;

methoxy$(C_2-C_4)$alkoxy, preferably methoxypolyethyleneoxy and methoxypolypropyleneoxy;

hydroxy$(C_2-C_4)$alkoxy, preferably 2-hydroxy-1-propyloxy and 2-hydroxy-3-butyloxy;

trichloroisobutyloxy;

$(C_2-C_4)$alkoxycarbonylalkyleneoxy, preferably ethoxycarbonylmethyleneoxy and butoxycarbonylmethyleneoxy.

The methoxy, ethoxy and n-butoxy groups are particularly preferably used.

In place of the alkoxy groups, hydrolyzable, physiologically acceptable alkylamino or aralkylamino groups are also suitable, such as, for example, the following groups:

hydroxy$(C_2-C_6)$alkylamino, preferably 2-hydroxyethylamino, tris(hydroxymethylene)methylamino and glycosylamino;

$(C_2-C_4)$alkanoyloxyethylamino, preferably 2-acetoxyethylamino and 2-butanoyloxyethylamino;

mercapto$(C_2-C_4)$alkylamino, preferably 2-mercaptoethylamino;

the methyl esters of natural $\alpha$-amino acids, preferably the methyl ester of phenylalanine and the methyl ester of leucine.

As indicated above, the group $R^1$ can be very variable, in particular since it only occurs as a side group in the actual polymer according to the invention. It can, for example, also be a hydroxyl group if copolyamides or polymer mixtures are employed.

By esterification of aminoethanol with the dicarboxylic acids of the citrate cycle, in particular succinic acid and fumaric acid, diamines which are employed according to the invention are likewise obtained. Furthermore, pharmacologically acceptable piperazines of the formula Ib can be used.

Dicarboxylic acids according to the invention are n-acylated glutamic acid and aspartic acid of the formula IIa whose amino group is protected by a $(C_2-C_4)$acyl group. Preferred acyl groups are acetyl and butyryl, in particular acetyl. The acyl groups can also have longer chains, but, with increasing chain length, it becomes more complicated to introduce them into the dicarboxylic acid. In addition, the reactivity of the carbonyl group in the $\alpha$-position is reduced by a longer-chain acyl group.

Furthermore, straight-chain, saturated or monounsaturated dicarboxylic acids having 2–10, preferably 4–8, particularly preferably 4–6 carbon atoms can also be used for the polycondensation. In this case, glutaric acid and fumaric acid are again very particularly preferred. It is furthermore possible to prepare, by esterification of these dicarboxylic acids with pharmacologically acceptable diols of the formula IIb or by amidation with diamines of the formula Ib, dicarboxylic acid compounds which can likewise be used according to the invention. Suitable diols are, for example, propanediol and ethylene glycol, and the polymers thereof having up to 100 repeating units. 2,3-butanediol is preferably used. In this connection, suitable diamines are piperazine and the physiologically acceptable methyl-homologs thereof. However, piperazine is preferably used.

The biologically degradable polyamides according to the invention are condensed by methods which are known per se (P. W. Morgan "Condensation Polymers: by Interfacial and Solution Methods", Interscience Publ., New York 1965). These products are easy to prepare by interfacial polycondensation of the free diamines with dicarboxylic acid chlorides or by solution polycondensation of the diamines or the bis-silyl derivatives thereof, with chlorides or active esters of the dicarboxylic acids in an aprotic dipolar solvent.

To this purpose, the diamino component is dissolved in water which contains excess diamine and organic or inorganic bases, such as, for example, trialkylamines or alkali metal hydroxides or alkali metal carbonates, as acid scavengers. The dicarboxylic acid component, preferably the dicarboxylic acid dichloride, is dissolved in water-immiscible organic solvents, such as, for example, aliphatic, cycloaliphatic and aromatic hydrocarbons, or halogenated aliphatic and aromatic hydrocarbon. This solution is added to the diamine solution with vigorous stirring, and the polymer produced is isolated by filtration or centrifugation. The polyamide is washed with water and ethanol or acetone and dried in vacuo at elevated temperature.

50% of the polyamide prepared in this fashion are repeating units of the diamino compounds and 50% are repeating units of the dicarboxylic acid compounds. Homopolymers can be built up, that is to say each one of the diamino compounds mentioned reacts with one of the dicarboxylic acid compounds mentioned, but also copolymeres in which two or more compounds from the group comprising the diamino compounds and two or more compounds from the group comprising the dicarboxylic acid compounds are contained can also be built up.

When using the amino compound of the general formula Ia and fumaric acid or a mixture of fumaric acid/glutaric acid as the dicarboxylic acid for the polycondensation, the corresponding products are open, via the ester function of the lysine or ornithine radical, to polymer-analogous reactions with amines, in particular with aminoethanol, or amino-functional pharmaceuticals, or, via the double bonds of the fumarate, are open to free-radical cross-linking. In this fashion, physical properties, for example solubility and hydrophilia, and physiological properties, such as stability towards hydrolytic degradation, tolerance or pharmacological activity, can subsequently be modified on the polymer.

The carbonyl or aminoacyl function which is in the α-position to the amide structure influences, by means of inductive and steric effects, the degradation of the polymer and the release of the active compound. For example, the hydrophilia of the polymer, and thus its swellability (water resorption) and solubility in the physiological environment, are increased by the carboxyl group produced after known enzymatic or hydrolytic ester cleavages in the body. The undesired, steep decrease in the liberation rate which occurs after the initial "burst effect" in the implant materials described is thereby compensated for.

From the polyamides according to the invention, implantable particles, in particular microcapsules and microspheres, and, by compacting macroscopic molded elements of any geometry, in particular tablets and rods, can be prepared by known methods.

The polyamide can be dissolved, for example, with the active compound in a suitable polar aprotic solvent, for example dimethyl sulfoxide or dimethylacetamide. The solution is emulsified, with addition of an emulsifier, into an oil phase at a temperature at which the polymer solution is liquefied. After several minutes, solidification of the individual solvent/polymer droplets is initiated by cooling the emulsion. The polymer beads are hardened by washing with a suitable solvent in which the solvent employed for dissolving the polyamide and the oil phase dissolve, but not the polymer droplets. The volume of the polymer beads is reduced during this, but the shape does not change.

The polyamides according to the invention can also be employed as mixtures and in blends with other biodegradable polymers or physiologically acceptable auxiliaries (for example polymer plasticizers).

In vitro degradation experiments with the polyamides according to the invention have shown that the degradation rate can be regulated in a controlled manner via the functional side groups.

The invention is described in detail in the following examples. Percentage data refer to the weight unless otherwise stated.

EXAMPLE 1

Preparation of poly(L-lysine ethyl ester fumaramide) (LEF)

0.76 g of fumaryl chloride in 100 ml of ethanol-free chloroform is added, with rapid stirring, to a solution of 2.47 g of L-lysine ethyl ester dihydrochloride and 2.12 g of sodium carbonate in 100 ml of ice-cold water. After stirring for ten minutes at room temperature, 100 ml of 1N hydrochloric acid are added, and the mixture is stirred for a further minute. The resultant polymer is filtered off under suction through a glass filter frit, and washed first with hot water, then with cold water and subsequently with acetone. After drying in vacuo over phosphorus pentoxide, 0.8–0.95 g (63–75% of theory) of white poly(L-lysine ethyl ester fumaramide) are obtained. ($M_w$ 23,000, water resorption 9.5% by weight, $T_G$ 75° C.).

EXAMPLE 2

Preparation of poly(L-lysine methyl ester fumaramide) (LMF)

0.76 g of fumaryl chloride is polycondensed with 2.34 g of L-lysine methyl ester dihydrochloride and analogously to Example 1. 0.8 g of white poly(L-lysine methyl ester fumaramide) (LMF) is obtained.

EXAMPLE 3

Preparation of poly(L-lysine butyl ester fumaramide) (LBF)

1.52 g of fumaryl chloride in 200 ml of methylene chloride, distilled over phosphorus pentoxide, are poured, with stirring with an Ultraturax, into a solution of 5.5 g of L-lysine butyl ester dihydrochloride and 4.24 g of sodium carbonate in 200 ml of ice-cold water. After stirring for two minutes with ice cooling, 100 ml of 1N hydrochloric acid are added, and the mixture is stirred for a further minute. The methylene chloride is expelled from the reaction mixture by passing in steam, and the polycondensate is subsequently filtered off under suction through a frit. After washing with hot water, cold water and ethanol, the polymer is dried in vacuo at 60° C. 1.8 g (64% of theory) of white, fibrous poly(L-lysine butyl ester fumaramide) are obtained.

EXAMPLE 4

Preparation of copoly(L-lysine methyl ester-piperazine fumaramide)

0.76 g of fumaryl chloride in 100 ml of methylene chloride is polycondensed, analogously to Example 2, with 1.2 g of L-lysine methyl ester dihydrochloride and 0.93 g of piperazine in 100 ml of water which contains 2.12 g of sodium carbonate. 0.7 g (69% of theory) of the copolyamide, which dissolves in concentrated sulfuric acid and formic acid, is obtained.

EXAMPLE 5

Preparation of copoly(L-lysine ethyl-butyl ester fumaramide)

1.52 g of fumaryl chloride in 200 ml of methylene chloride are polycondensed, analogously to Example 2, with 2.47 g of lysine ethyl ester dihydrochloride and 2.75 g of lysine butyl ester dihydrochloride in 200 ml of water which contains 5.5 g of potassium hydroxide. 2.5 g (71% of theory) of white, fiber-like copolycondensate are obtained.

EXAMPLE 6

(LMEF 75/25)

1.52 g of fumaryl chloride are polycondensed, analogously to Example 4, with 3.45 g of lysine methyl ester dihydrochloride and 1.30 g of lysine ethyl ester dihydrochloride. 2.0 g (70% of theory) of a white, fiber-like copolycondensate are obtained.

EXAMPLE 7

Preparation of poly(diethylene succinate fumaramide)

1.75 g of di-N-hydroxybenzotriazole fumarate and 1.02 g of 2-aminoethyl succinate in 10 ml of dry N-methylpyrrolidone are stirred at room temperature for 48 hours with exclusion of moisture. The reaction mixture is subsequently added dropwise to 100 ml of water, and the polycondensate is centrifuged off and, after washing with hot water, dried in vacuo at 60° C.

0.7 g (49% of theory) of polymer are obtained as a sticky, viscous material.

EXAMPLE 8

(LMFG 50/50)

Preparation of poly(L-lysine methyl ester fumaramide/L-lysine methyl ester glutaramide) Copolymer 50:50 (LMFG 50:50)

0.7 g of glutaryl dichloride and 0.84 g of fumaryl dichloride are dissolved in 170 ml of $CH_2Cl_2$. This solution is added at room temperature with vigorous stirring to a solution of 2.91 g of L-lysine methyl ester and 3.0 g of $Na_2CO_3$ in 120 ml of $H_2O$. The polycondensation, which occurs suddenly, is terminated after 15 minutes by adding 120 ml of 1N aqueous HCl. The methylene chloride is then expelled by passing in steam. The hot aqueous mixture is filtered, and the solid product is washed several times with water and triturated with boiling ethanol. Yield: 1.3 g (60% of theory) after vacuum drying (20 hours).

EXAMPLE 9

(LMFG 60/40)

Preparation of poly(L-lysine methyl ester fumaramide/L-lysine methyl ester glutaramide) Copolymer 60:40 (LMFG 60:40)

0.56 g of glutaryl dichloride and 0.77 g of fumaryl dichloride are dissolved in 170 ml of $CH_2Cl_2$ and polycondensed, as described in Example 7, with a solution of 2.91 g of L-lysine methyl ester and 3 g of $Na_2CO_3$ in 120 ml of $H_2O$.

Yield: 1.3 g (60% of theory).

EXAMPLE 10

Preparation of monolithic microspheres from LEF 460 mg of octadecanol are dissolved in 100 ml of viscous paraffin (Riedel de Haen) by ultrasound treatment, warmed to 50° C. and stirred. 70 mg of LEF, which has been prepared according to Example 1, and 30 mg of LHRH-analogous peptide hormone are dissolved in dimethyl sulfoxide by ultrasound treatment. The solution is added dropwise to the stirred paraffin solution, and the mixture is emulsified for 10 minutes.

The emulsion is stirred into 300 ml of n-butanol at 40° C., the paraffin matrix dissolving and the polymer beads precipitating. After about 6 hours, the supernatant liquid is decanted off, and the polymer beads are taken up in 100 ml of butanol, hardened for 16 hours and then centrifuged off. Polymer beads having a size distribution between 20 and 100 µm are obtained.

EXAMPLE 11

Preparation of monolithic microspheres from LMFG 60:40 (from Example 9)

90 mg of LMFG 60:40 from Example 9 are dissolved in small portions in 1 ml of dimethyl sulfoxide. The solution is added dropwise to about 50 ml of liquid nitrogen from a syringe with a fine cannula (external cannula diameter 0.4–1.2 mm: depending on the desired bead size). The frozen beads thus produced are separated from the nitrogen by decanting and added to about 500 ml of water. After 2 hours, the DMSO has diffused out of the beads, and the beads have hardened. They are freeze-dried for 20 hours.

EXAMPLE 12

Preparation of microspheres with active compound 56 mg of LMF from Example 2 and 14 mg of $^R$Pluronic F 68 (manufacturer Fluka AG, Neu-Ulm) are dissolved in 1 ml of dimethyl sulfoxide at 50° C. 30 mg of buserelin (manufacturer Behringwerke AG, Marburg) are then dissolved by brief treatment with ultrasound. The polymer and active compound solution is added dropwise to a prepared amount of liquid nitrogen (100 ml) using a cannula (disposable syringe, external cannula diameter 0.6 mm).

The resultant microspheres are transferred into 200 ml of water, and the residual solvent is extracted for 2 hours. Excess water is decanted off and the microspheres are lyophilized (diameter after lyophilization 1–2 mm).

EXAMPLE 13

Preparation of microspheres 70 mg of LMF from Example 2 and 30 mg of maize starch SF type Snowflake 05063 (manufacturer Maizena Industrieprodukte GmbH, Hamburg) are dissolved in 1 ml of dimethyl sulfoxide at 50° C. The polymer solution is added dropwise to a prepared amount of liquid nitrogen (100 ml) using a cannula (disposable syringe, external cannula diameter 0.6 mm).

The resultant microspheres were transferred into 200 ml of water, the residual solvent was extracted for 2 hours, and the microspheres were lyophilized (diameter after lyophilization 1–2 mm).

EXAMPLE 14

Degradation experiments 5 samples each of 100 mg of poly(lysine ethyl fumaramide), which has been prepared according to Example 1, are in each case introduced into a semimicro dialysis tube made from regenerated cellulose (Spectra/Por No. 132600, Spectrum Medical Ind., Inc., L.A., U.S.A.). The tube segments (length 80 mm, flat width 2.5 mm) are sealed with a wire loop and incubated, with stirring, in a phosphate buffer solution comprising 0.00205 mol of $Na_2HPO_4$ and 0.0045 mol of $NaH_2PO_4$ (pH 7.4) at 37° C. and a partial pressure of oxygen of 50 mm Hg.

0.108 mol of NaCl and 0.030 mol of $NaHCO_3$ are added to the phosphate buffer, which is then stabilized against attack by microorganisms by 0.0078 mol of $NaN_3$. The buffer is exchanged with a throughput of 50 ml/d.

Over a period of 120 days, a sample is taken after each 30 days and washed with distilled water, and the degradation behavior, as shown in the following table, characterized as follows by means of the polymer remaining:

(a) dry weight after storage for 50 hours in vacuo over $P_2O_5$ (b) water resorption after storage for 74 hours at a relative atmospheric humidity of 92%

(c) molecular weight (about $M_w$) by gel permeation chromatography in dimethyl sulfoxide with the aid of an allyl dextran ($^R$Sephacryl S-200, Pharmacia, Uppsala) which is covalently crosslinked with N,N'-methylene bisacrylamide.

| Days | 30 | 60 | 90 | 120 |
|---|---|---|---|---|
| Dry Weight (mg) | 85 | 79 | 68 | 55 |
| Water resorption | 17 | 25 | 32 | 38 |

-continued

| Days | 30 | 60 | 90 | 120 |
|---|---|---|---|---|
| (% by weight) | | | | |
| Molecular weight (Dalton) | 25000 | 22000 | 20000 | 19000 |

EXAMPLE 15

The water resorption (% by weight) of various homopolyamides and copolyamides after storage for 74 hours at a relative atmospheric humidity of 92% and the duration of hydrolysis of the alkyl ester sidegroup (hours) until complete solubilization of each 100 mg of polymer powder in 10 ml of aqueous NaOH (pH 13) are determined.

| Polyamide | according to Example | water resorption | duration of solubilization [h] |
|---|---|---|---|
| Poly(lysine methyl ester fumaramide) | 2 | 13.8 | 3 |
| Poly(lysine ethyl ester fumaramide) | 1 | 9.2 | 48 |
| Poly(lysine butyl ester fumaramide) | 3 | 5.7 | 864 |
| Poly(lysine methyl/ethyl ester fumaramide) | | | |
| Molar proportion of comonomers 75:25 molar | 6 | 10.1 | 30 |
| Molar proportion of comonomers 25:75 molar | 6 | 9.7 | 55 |
| Poly(lysine ethyl/butyl ester fumaramide): | | | |
| Molar proportion of comonomers 75:25 molar | 5 | 8.2 | 528 |
| Molar proportion of comonomers 50:50 molar | 5 | 7.0 | 696 |

EXAMPLE 16

Polymer degradation

The water resorption (in % by weight) after storage for 74 hours at a relative atmospheric humidity of 92% and the duration of hydrolysis of the side groups (in hours) until complete solubilization of each 100 mg of polymer powder in 100 ml of aqueous NaOH (pH 13) are determined.

The degradation in buffer at the physiological pH is carried out as follows.

In each case 500 mg of polymer are incubated in 30 ml of a phosphate buffer solution comprising 0.00205 mol of $Na_2HPO_4$ and 0.0045 mol of $NaH_2PO_4$ (pH 7.4) and stirred at 37° C. in sealed glass bottles (50 ml).

The phosphate buffer is stabilized against microbial attack using 0.0078 mol of $NaN_3$, and the pH is adjusted after each 7 days.

After a period of 150 days, the weight losses of the polymer samples are measured: the buffer solution with incubated polymer is filtered through a tared glass frit, the residue is dried for 24 hours in vacuo over phosphorus pentoxide, and the weight loss is determined.

| Polymer | according to Example | water resorption, % | solubilization, h | weight loss, % |
|---|---|---|---|---|
| LMF | 2 | 14 | 3 | 21 |
| LMFG 60/40 | 9 | 18 | 1 | 38 |
| LEF | 1 | 9 | 48 | 6 |
| LMEF 75/25 | 6 | 10 | 30 | 9 |
| LMF/Pluronic F 68 | 12 | 16 | 0.5 | 55 |
| LMF/starch SF | 13 | 18 | 1 | 43 |

EXAMPLE 17

Release of buserelin from LMF/Pluronic F 68/buserelin microspheres from Example 12

The microspheres investigated have the composition: 12% by weight of buserelin, 25% by weight of Pluronic F 68 and 63% by weight of LMF.

The release of active compound in a buffer solution was measured by UV spectroscopy. (BUffer: 2.91 g of $Na_2HPO_4$; 0.540 g of $NaH_2PO_4$; 0.4 g of $NaN_3$, 6.328 g of NaCl; 2.52 g of $NaHCO_3$ in 1 liter of water). In the figure, the total released amount of buserelin is shown in % as a function of the time (in days).

We claim:

1. A biologically degradable polyamide having a polyamide backbone of recurring amide units, said polyamide having attached thereto, in the α-position to at least one said recurring amide unit, at least one functional group capable of controlling degradation and thereby capable of controlling the release of an active compound accompanying said polyamide, which polyamide is produced from at least one diamine (I) and at least one dicarboxylic acid (II) wherein the diamine (I) is at least one repeating unit of a diamino group selected from the group consisting of a monomeric compound of the formula Ia,

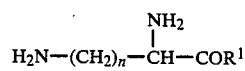

in which
R[1] is a physiologically acceptable, hydrolyzable alkoxy group, having up to 18 carbon atoms, which is unsubstituted or substituted by physiologically acceptable side groups, or is a physiologically acceptable, hydrolyzable alkylamino or aralkylamino group, or is a hydroxyl group, and n is 3 or 4, a monomeric compound which is produced by esterification of aminoethanol with a dicarboxylic acid of the tricarboxylic acid cycle, and a monomeric compound of the formula Ib,

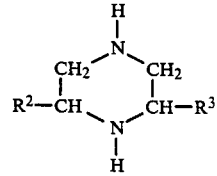

in which
R[2] and R[3], independently of one another, are hydrogen or methyl, and wherein the dicarboxylic acid (II) is at least one repeating unit of a dicarboxylic acid selected from the group consisting of a monomeric compound of the formula IIa,

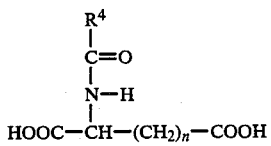

in which

R$^4$ is an alkyl group having 1 to 3 carbon atoms, and n is 1 or 2, a monomeric straight-chain, saturated or mono-unsaturated dicarboxylic acid having 2–10 carbon atoms, and a monomeric compound which is produced by esterification of at least one dicarboxylic acid of the tricarboxylic acid cycle with at least one diol of the formula IIb,

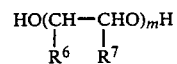

in which

R$^6$ and R$^7$, independently of one another, are hydrogen or a methyl group, and m is a number in the range 1 to 100, or by amidation with at least one diamine of the formula Ib, at least one of said diamine (I) and said dicarboxylic acid (II) supplying said functional group.

2. A polyamide as claimed in claim 1, wherein R$^1$ is n- or iso($C_1$–$C_{18}$)alkoxy, methoxy($C_2$–$C_4$)alkoxy, hydroxy($C_2$–$C_4$)alkoxy, ($C_2$–$C_4$)alkoxycarbonylalkyleneoxy, trichloroisobutoxy, hydroxy($C_2$–$C_6$)alkylamino, ($C_2$–$C_4$)alkanoyloxyethylamino, mercapto($C_2$–$C_4$)alkylamino or an amide of a naturally occurring α-amino acid.

3. A polyamide as claimed in claim 1, wherein R$^1$ is a methoxy, ethoxy or n-butoxy group.

4. A polyamide as claimed in claim 1, wherein the dicarboxylic acid employed is a straight-chain, saturated or monounsaturated dicarboxylic acid having 4–8 carbon atoms.

5. A polyamide as claimed in claim 1, wherein the dicarboxylic acid employed is fumaric acid or glutaric acid.

6. A polyamide as claimed in claim 1, wherein the diol of the formula IIb is 2,3-butanediol.

* * * * *